United States Patent [19]

Sannohe et al.

[11] Patent Number: 4,639,521

[45] Date of Patent: Jan. 27, 1987

[54] ISOQUINOLINE DERIVATIVES

[75] Inventors: Kunio Sannohe; Kengo Otsuka; Toshohiko Ito, all of Kanagawa; Masahiko Maruyama, Chiba; Takafumi Kitano, Chiba; Makoto Hirayama, Chiba, all of Japan

[73] Assignee: Mitsui Toatsu Chemicals, Inc., Tokyo, Japan

[21] Appl. No.: 878,527

[22] Filed: Jun. 20, 1986

[30] Foreign Application Priority Data

Jul. 2, 1985 [JP] Japan .................................. 60-144008

[51] Int. Cl.⁴ ................... C07D 401/04; C07D 217/24
[52] U.S. Cl. ...................................... 546/141; 516/15; 516/340; 549/341
[58] Field of Search .......................................... 546/141

[56] References Cited

U.S. PATENT DOCUMENTS 2,759,936  8/1956  Specter ................................ 546/141
3,480,634  11/1969  Finnelstein .......................... 546/141

*Primary Examiner*—Glennon H. Hollrah
*Assistant Examiner*—James H. Turnipseed
*Attorney, Agent, or Firm*—Browdy and Neimark

[57]  ABSTRACT

Isoquinoline derivatives represented by the general formula (I):

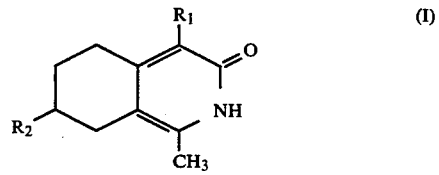

wherein $R_1$ denotes a hydrogen or halogen atom, or a nitro or acetyl group, and $R_2$ denotes a hydrogen atom, or a methyl, methoxy, phenyl, 4-pyridyl or 2-pyridyl group, and therapeutically acceptable salts thereof have high cardiotonic activity and low toxicity.

5 Claims, No Drawings

ISOQUINOLINE DERIVATIVES

FIELD OF THE INVENTION

The present invention relates to novel isoquinoline derivatives and therapeutically acceptable addition salts thereof. These isoquinoline derivatives and their addition salts are useful for cardiotonic agents.

PRIOR ART

In the treatment of heart failure, digitalis preparations, such as digoxin, digitoxin, and the like, have been used as cardiotonic agents: see, for example, "IYAKU-HIN YORAN (Summary of Pharmaceuticals)", 1977, YAKUGYO JIHO-SHA, Tokyo, Japan, pp. 324–327. On the other hand, different compounds having cardiotonic activity have also been reported: for example, nicotinonitrile derivatives in e.g. Japanese Patent Application Laying-open No. 57-70868, imidazolone derivatives in e.g. Japanese Patent Application Laying-open No. 59-155368, dihydropyridazinone derivatives in e.g. Japanese Patent Application Laying-open No. 58-74679.

PROBLEMS TO BE SOLVED BY THE INVENTION

The digitalis preparations presently used in the treatment require skill on being administered due to their narrow safety margin. Also, there is a problem of side-effect such as arrhythmia. On the other hand, the recently reported nicotinonitrile, imidazolone and dihydropyridazinone derivatives have a number of disadvantages, such as low cardiotonic activity, narrow safety margin, increase in the number of myocardial rhythm upon administration thereof, and high animal toxicity.

MEANS FOR SOLVING THE PROBLEMS

The present inventors have intensively studied for the purpose of providing cardiotonic compounds having wide safety margin and no side-effect, and now found that specific isoquinoline derivatives have high cardiotonic activity and low toxicity. Thus, the present invention has been attained.

Particularly, the isoquinoline derivatives according to the present invention are represented by the general formula (I):

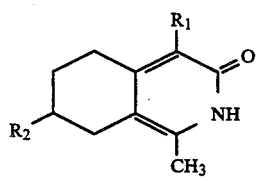

wherein $R_1$ denotes a hydrogen or halogen atom, or a nitro or acetyl group, and $R_2$ denotes a hydrogen atom, or a methyl, methoxy, phenyl, 4-pyridyl or 2-pyridyl group, and also include therapeutically acceptable salts thereof.

The compounds (I) of the present invention may also be tautomers thereof represented by the general formula (II):

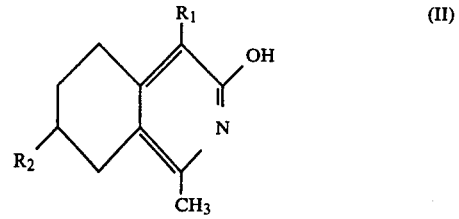

These compounds (II) are of course included within the scope of the present invention.

The isoquinoline derivatives of the present invention may be prepared by, for example, the following processes:

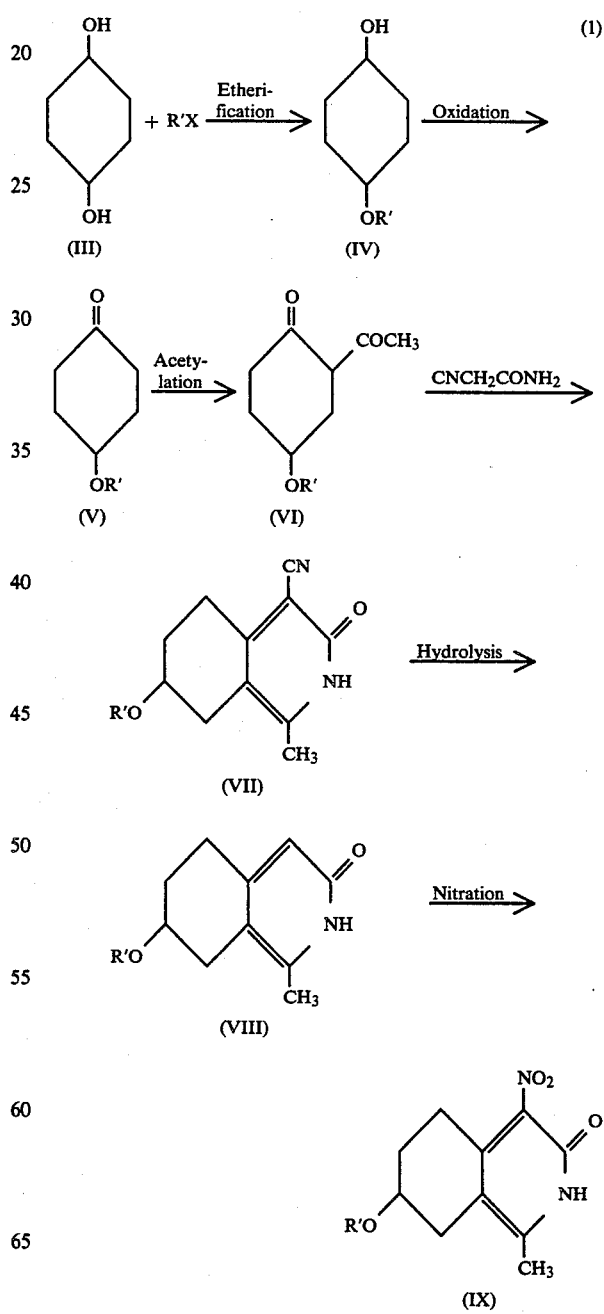

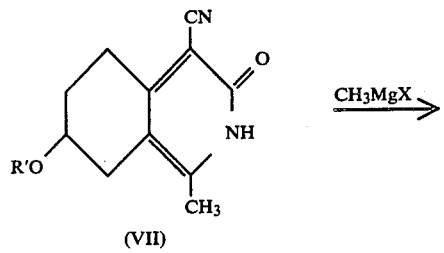
(VII)
CH₃MgX →
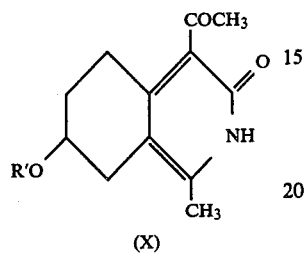
(X)
(3)
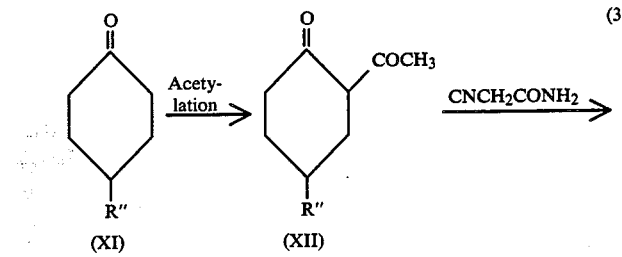
(XI) Acetylation → (XII) CNCH₂CONH₂ →
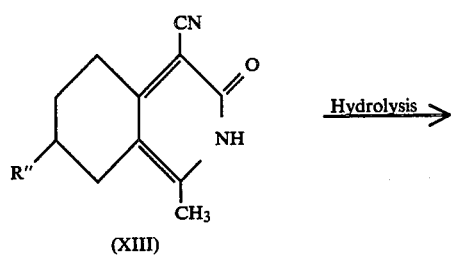
(XIII) Hydrolysis →
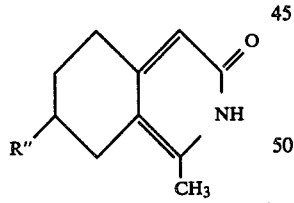
(XIV)
Nitration ↓
CH₃MgX ↓
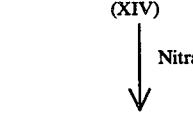
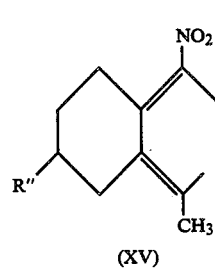
(XVI) (XV)
(2)
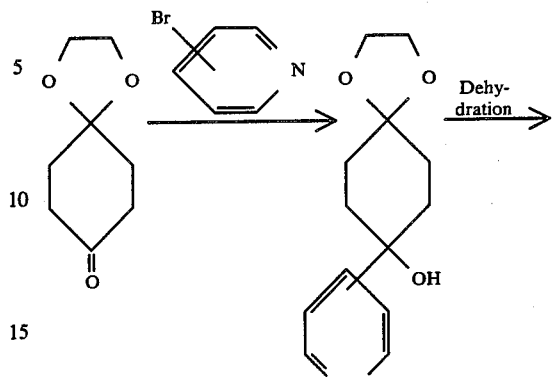
(XVII) → (XVIII) Dehydration →
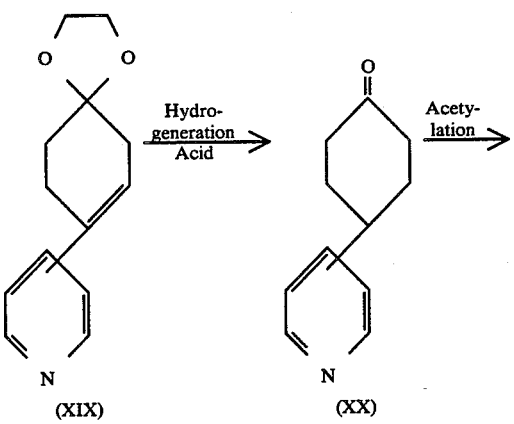
(XIX) Hydrogenation Acid → (XX) Acetylation →
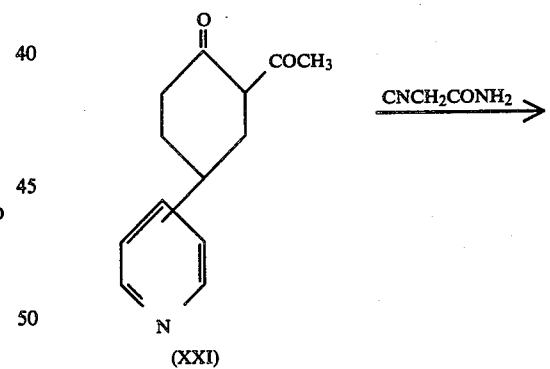
(XXI) CNCH₂CONH₂ →
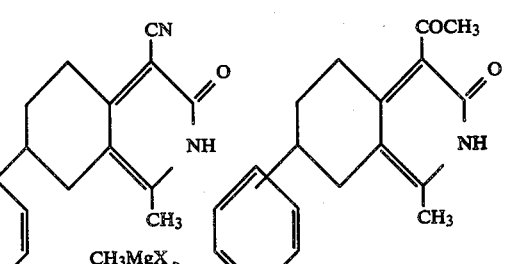
(XXII) CH₃MgX → (XXV)
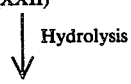
Hydrolysis ↓

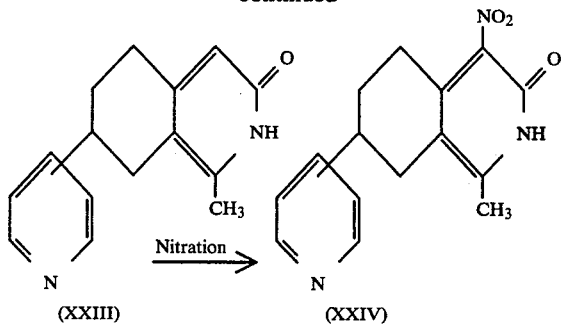

In the reaction routes (1) to (4) illustrated above, R' represents methyl group, X represents a halogen atom, and R" represents methyl or phenyl group.

In accordance with the reaction route (1), monoethers (IV) prepared from starting compounds (III) may be converted into (V) by the action of an oxidizing agent, such as pyridinium chlorochromate or manganese dioxide. Compounds (V) may then be acetylated to produce (VI) by using an appropriate acetylating agent, such as acetylimidazole, acetic anhydride, an acetyl halide, or an acetic acid ester, in the presence of a sodium alkoxide, sodium hydride, boron trifluoride acetate, lithium diisopropylamide, zinc chloride, or the like. Alternatively, (V) may be converted into enamines with cyclic amines such as pyrrolidine, and the enamines may then be acetylated by acetic anhydride to prepare (VI). Thereafter, compounds (VI) and cyanoacetamide may be subjected to condensation reaction in an alcohol, such as methanol or ethanol, in the presence of either a secondary amine such as, for example, piperidine or diethylamine, or a sodium alkoxide to prepare (VII). Then, (VII) may be reacted with a mineral acid such as sulfuric acid to produce compounds (VIII), which are included within the compounds (I) according to the present invention. The compounds (VIII) may further be nitrated in a conventional manner to prepare compounds (IX) having nitro group at 4-position thereof, which are also included within the compounds (I) according to the present invention.

In accordance with the reaction route (2), compounds (VII) may be reacted with a methylmagnesium halide to prepare compounds (X) having acetyl group at 4-position thereof, which are also included within the compounds (I) according to the present invention.

In accordance with the reaction route (3), other starting compounds (XI) may be treated by methods analogous to those in the reaction routes (1) and (2) to produce compounds (XIV), (XV) and (XVI) having hydrogen atom, nitro group and acetyl group, respectively, at 4-position thereof. These compounds (XIV), (XV) and (XVI) are also included within the compounds (I) according to the present invention.

In accordance with the reaction route (4), still other starting compounds (XVII) may be condensed with 2- or 4-bromopyridine in the presence of n-butyl lithium or the like to prepare (XVIII), which may then be subjected to the action of, e.g., thionyl chloride in pyridine to produce (XIX). Then, (XIX) may be reduced with hydrogen in a mineral acid to prepare (XX), which may be treated by methods analogous to those in the reaction routes (1) and (2) to produce compounds (XXIII), (XXIV) and (XXV) having hydrogen atom, nitro group and acetyl group, respectively, at 4-position thereof. The compounds (XXIII), (XXIV) and (XXV) are also included within the compounds (I) according to the present invention.

Further, compounds having a halogen atom at 4-position thereof, which are also included within the scope of the present invention, may be prepared by reacting, e.g., the compounds represented by the aforementioned formula (VIII), (XIV) or (XXIII) with an appropriate halogenating agent such as bromine in a solvent such as acetic acid.

When the compounds according to the present invention are employed as cardiotonic agents, they may be administered parenterally, for example intravenously, but preferably orally. The compounds according to the present invention may be prepared into any dosage form suitable for intended administration route. For example, the compounds and salts thereof can be used either as such or in combination with any pharmaceutically acceptable, innoxious adjuvant(s), such as excipient, carrier, binder, stabilizer, diluent, and flavors. The dosage form of these agents may be tablet, capsule, granule, powder, syrup, or elixir when they are orally administered, or injectable preparations when administered parenterally.

Dosage amounts to be administered to human beings may be determined by physicians by taking into consideration conditions and ages of patients to be treated and administration routes of the agents to them, etc. For example, the dosage amounts may be about 0.1–10 mg per kg of body weight a day for oral administration, but of course they are not limited to these.

ADVANTAGES OF THE INVENTION

According to the present invention there are provided novel isoquinoline derivatives. The novel isoquinoline derivatives of the present invention have been found to be useful for cardiotonic agents and have low toxicity and wide safety margin. Their utility as cardiotonic agents is proved by their effective activity in the standard pharmacological test methods. For example, significant recovery is observed in cardiac function under anesthesia which has been lowered by intravenous injection of propranolol.

The present invention will be illustrated in detail with reference to the following examples and test examples.

EXAMPLE 1

2,3,5,6,7,8-Hexahydro-1-methyl-3-oxo-7-(4-pyridyl)isoquinoline (1) 4-Hydroxy-4-(4-pyridyl)cyclohexanone ethyleneacetal Twenty milliliters (ml) of 1.6M solution of n-butyl lithium in hexane was added to 35 ml of ether cooled at −78° C. Five grams (g) of 4-bromopyridine dissolved in 30 ml of ether was added. Then, a solution of 5 g of 1,4-cyclohexanedione monoethyleneacetal dissolved in 30 ml of tetrahydrofuran was added. After the reaction was completed, the reaction mixture was poured into a saturated aqueous solution of ammonium chloride and extracted with chloroform and purified. There was obtained 5 g of 4-hydroxy-4-(4-pyridyl)cyclohexanone ethyleneacetal.

Melting point (mp): 165.5°–167.5° C.

NMR $\delta_{TMS}^{CDCl_3}$: 1.6–2.2 (8H, m); 3.9 (1H, s); 4.00 (4H, s); 7.45 (2H, dd); 8.44 (2H, dd).

(2) 4-(4-Pyridyl)cyclohex-3-enone ethyleneacetal

To 5 g of 4-hydroxy-4-(4-pyridyl)cyclohexanone ethyleneacetal dissolved in 40 ml of pyridine, there was added 8 ml of thionyl chloride at −10° C. After stirring the mixture at 0° C., the reaction mixture was poured into ice water. Then, an excess amount of aqueous sodium hydroxide solution was added. The reaction mixture was extracted with methylene chloride and purified. Thus, there was obtained 4 g of 4-(4-pyridyl)cyclohex-3-enone ethyleneacetal.

mp:67°–70° C.

NMR $\delta_{TMS}^{CDCl_3}$: 1.86 (2H, t); 2.4–2.7 (4H, m); 4.04 (4H, s); 6.24 (1H, t); 7.28 (2H, d); 8.52 (2H, d).

(3) 4-(4-Pyridyl)cyclohexanone 4-(4-Pyridyl)cyclohex-3-enone ethyleneacetal (4 g) was dissolved in 70 ml of 0.5N hydrochloric acid. To the solution, there was added 400 mg of 10% palladium-carbon. Hydrogenation was carried out at room temperature under atmospheric pressure. After removing out the catalyst and adding an aqueous sodium hydroxide solution to alkalify, the reaction mixture was extracted with methylene chloride to obtain 2.7 g of 4-(4-pyridyl)cyclohexanone.

NMR $\delta_{TMS}^{CDCl_3}$: 1.7–2.3 (4H, m); 2.4–2.6 (4H, m); 2.8–3.2 (1H, m); 7.15 (2H, d); 8.51 (2H, d).

(4) 2-Acetyl-4-(4-pyridyl)cyclohexanone

To a solution of 3.2 ml of diisopropylamine dissolved in 40 ml of tetrahydrofuran, there was added 14.2 ml of 1.6M solution of n-butyl lithium in hexane at −20° C. Then, a solution of 2 g of 4-(4-pyridyl)cyclohexanone dissolved in 40 ml of tetrahydrofuran was added at −40° C. The reaction mixture was cooled to −78° C., and 2.5 g of acetylimidazole dissolved in 40 ml of tetrahydrofuran was added. The reaction mixture was stirred at room temperature, poured into ice water, and then washed with ether. The aqueous layer was saturated with ammonium chloride and extracted with methylene chloride. Thus, there was obtained 1.65 g of 2-acetyl-4-(4-pyridyl)cyclohexanone.

NMR $\delta_{TMS}^{CDCl_3}$: 1.7–2.2 (3H, m); 2.16 (3H, s); 2.3–2.6 (3H, m); 2.6–2.9 (1H, m); 7.10 (2H, dd); 8.55 (2H, dd); 15.7 (1H, s).

(5) 4-Cyano-2,3,5,6,7,8-hexahydro-1-methyl-3-oxo-7-(4-pyridyl)isoquinoline

2-Acetyl-4-(4-pyridyl)cyclohexanone (1.65 g) and cyanoacetamide (0.64 g) were dissolved in ethanol, and a small amount of piperidine was added. The reaction mixture was heated under reflux for 7 hours. After the reaction was completed, deposited crystals were filtered out to obtain 0.7 g of 4-cyano-2,3,5,6,7,8-hexahydro-1-methyl-3-oxo-7-(4-pyridyl)isoquinoline.

mp: 310° C. (decomposition).

NMR $\delta_{TMS}^{DMSO-d_6}$: 1.7–2.1 (2H, m); 2.22 (3H, s); 2.3–2.7 (2H, m); 2.8–3.0 (3H, m); 7.35 (2H, dd); 8.50 (2H, dd).

(6) 2,3,5,6,7,8-Hexahydro-1-methyl-3-oxo-7-(4-pyridyl)isoquinoline

4-Cyano-2,3,5,6,7,8-hexahydro-1-methyl-3-oxo-7-(4-pyridyl)isoquinoline (0.5 g) was dissolved in 85% sulfuric acid, and the solution was heated under reflux at 180°–200° C. for 5 hours. After cooling the reaction mixture was poured into ice water. Deposited crystals were filtered out and then purified to obtain 0.38 g of 2,3,5,6,7,8-hexahydro-1-methyl-3-oxo-7-(4-pyridyl)isoquinoline.

mp>300° C.

NMR $\delta_{TMS}^{CF_3COOH}$: 2.0–3.8 (7H, m); 2.64 (3H, s); 7.10 (1H, s); 8.0–8.2 (2H, m); 8.7–8.9 (2H, m).

EXAMPLE 2

2,3,5,6,7,8-Hexahydro-1-methyl-4-nitro-3-oxo-7-(4-pyridyl)isoquinoline 2,3,5,6,7,8-Hexahydro-1-methyl-3-oxo-7-(4-pyridyl)isoquinoline (0.5 g) obtained by the method described in Example 1 (6) was added into a mixture of 3 ml of 60% nitric acid and 1 ml of concentrated sulfuric acid at 5°–8° C., and the resultant mixture was agitated for one hour. The reaction was then allowed to proceed at room temperature for 4 hours. After the reaction was completed, the reaction mixture was added into ice water. Precipitated crystals were filtered out and then purified. Thus, there was obtained 0.135 g of 2,3,5,6,7,8-hexahydro-1-methyl-4-nitro-3-oxo-7-(4-pyridyl)isoquinoline.

mp: 275°–276° C. (decomposition).

NMR $\delta_{TMS}^{DMSO-d_6}$: 2.00 (2H, m); 2.14 (3H, s); 2.70 (5H, m); 7.40 (4H, m); 12.56 (1H, s).

EXAMPLE 3

4-Acetyl-2,3,5,6,7,8-hexahydro-1-methyl-3-oxo-7-(4-pyridyl)isoquinoline

Magnesium (0.23 g) was added to 10 ml of ether, and a solution consisting of 1.9 g of methyl iodide and 2 ml of ether was dropwise added under reflux. Then, 0.5 g of 4-cyano-2,3,5,6,7,8-hexahydro-1-methyl-3-oxo-7-(4-pyridyl)isoquinoline obtained in Example 1 (5) was added and thereafter 20 ml of tetrahydrofuran was also added. The reaction mixture was refluxed for 8 hours and cooled. Hydrochloric acid was added to acidify and the reaction mixture was allowed to stand overnight. Precipitated crystals were filtered out and purified to obtain 0.13 g of 4-acetyl-2,3,5,6,7,8-hexahydro-1-methyl-3-oxo-7-(4-pyridyl)isoquinoline.

mp: 296°–301° C. (decomposition).

NMR $\delta_{TMS}^{DMSO-d_6}$: 1.6–2.2 (2H, m); 2.2 (3H, s); 2.43 (3H, s); 2.5–3.0 (5H, m); 7.25–7.45 (2H, m); 8.45–8.62 (2H, m); 11.9 (1H, s).

IR $\nu_{max}^{KBr}$ cm$^{-1}$: 2880, 1635, 1605, 1535, 1475, 1420, 1180.

EXAMPLE 4

2,3,5,6,7,8-Hexahydro-1-methyl-3-oxo-7-(2-pyridyl)isoquinoline

(1) 4-Hydroxy-4-(2-pyridyl)cyclohexanone ethyleneacetal

4-Bromopyridine used in Example 1 (1) was replaced by 5 g of 2-bromopyridine, which was treated as in Example 1 (1) for 4-bromopyridine. There was obtained 4.7 g of 4-hydroxy-4-(2-pyridyl)cyclohexanone ethyleneacetal.

NMR $\delta_{TMS}^{CDCl_3}$: 1.5–1.9 (4H, m); 1.9–2.4 (4H, m); 3.96 (4H, s); 7.2 (1H, dd); 7.4 (1H, d); 7.68 (1H, ddd); 8.48 (1H, dd).

(2) 4-(2-Pyridyl)cyclohex-3-enone ethyleneacetal

4-Hydroxy-4-(2-pyridyl)cyclohexanone ethyleneacetal (4.6 g) was used and treated as in Example 1 (2).

There was obtained 3.3 g of 4-(2-pyridyl)cyclohex-3-enone ethyleneacetal.

NMR $\delta_{TMS}^{CDCl_3}$: 1.92 (2H, t); 2.4–2.56 (2H, m); 2.64–2.82 (2H, m); 3.96 (4H, s); 6.44–6.60 (1H, m); 7.12 (1H, dd); 7.36 (1H, d); 7.58 (1H, ddd); 8.52 (1H, dd).

(3) 4-(2-Pyridyl)cyclohexanone 4-(2-Pyridyl)cyclohex-3-enone ethyleneacetal (3.3 g) was used and treated as in Example 1 (3). There was obtained 2.2 g of 4-(2-pyridyl)cyclohexanone.

NMR $\delta_{TMS}^{CDCl_3}$: 1.8–2.6 (8H, m); 3.0–3.32 (1H, m); 7.0–7.3 (2H, m); 7.62 (1H, ddd); 8.48 (1H, dd).

(4) 2-Acetyl-4-(2-pyridyl)cyclohexanone 4-(2-Pyridyl)cyclohexanone (2.2 g), pyrrolidine (2 g) and benzene (20 ml) were mixed and refluxed for 3 hours to dehydrate. After distilling out benzene, there was obtained enamine of 4-(2-pyridyl)cyclohexanone and pyrrolidine. The enamine was dissolved in 20 ml of dioxane. Then, 3 g of acetic anhydride was added and the mixture was allowed to stand overnight. After adding 10 ml of water, the mixture was refluxed for one hour and cooled. An aqueous solution of sodium hydroxide was added to alkalify and the reaction mixture was extracted with methylene chloride. All of the thus obtained crude product 2-acetyl-4-(2-pyridyl)cyclohexanone was directly used in the following step.

(5) 4-Cyano-2,3,5,6,7,8-hexahydro-1-methyl-3-oxo-7-(2-pyridyl)isoquinoline

2-Acetyl-4-(2-pyridyl)cyclohexanone was used and treated as in Example 1 (5). There was obtained 0.76 g of 4-cyano-2,3,5,6,7,8-hexahydro-1-methyl-3-oxo-7-(2-pyridyl)isoquinoline.

mp>300° C.

NMR $\delta_{TMS}^{DMSO-d_6}$: 1.8–2.2 (2H, m); 2.24 (3H, s); 2.4–2.6 (2H, m); 2.8–3.1 (3H, m); 7.2–7.5 (2H, m); 7.76 (1H, m); 8.54 (1H, m); 12.3 (1H, s).

(6) 2,3,5,6,7,8-Hexahydro-1-methyl-3-oxo-7-(2-pyridyl)isoquinoline

4-Cyano-2,3,5,6,7,8-hexahydro-1-methyl-3-oxo-7-(2-pyridyl)isoquinoline was used and treated as in Example 1 (6). Thus, 2,3,5,6,7,8-hexahydro-1-methyl-3-oxo-7-(2-pyridyl)isoquinoline was obtained.

mp: 260° C.

NMR $\delta_{TMS}^{DMSO-d_6}$: 1.6–2.2 (2H, m); 2.12 (3H, s); 2.4–3.2 (5H, m); 5.98 (1H, s); 7.18–7.42 (2H, m); 7.65–7.88 (1H, m); 8.45–8.60 (1H, m); 11.35 (1H, s).

EXAMPLE 5

4-Acetyl-2,3,5,6,7,8-hexahydro-1-methyl-3-oxo-7-(2-pyridyl)isoquinoline

4-Cyano-2,3,5,6,7,8-hexahydro-1-methyl-3-oxo-7-(2-pyridyl)isoquinoline obtained in Example 4 (5) was treated in a similar manner to that of Example 3. There was obtained 4-acetyl-2,3,5,6,7,8-hexahydro-1-methyl-3-oxo-7-(2-pyridyl)isoquinoline.

mp: 254°–256° C.

NMR $\delta_{TMS}^{DMSO-d_6}$: 1.6–2.2 (2H, m); 2.28 (3H, s); 2.42 (3H, s); 2.4–3.2 (5H, m); 7.2–7.5 (2H, m); 7.7–8.0 (1H, m); 8.5–8.6 (1H, m); 11.9 (1H, s).

EXAMPLE 6

4-Acetyl-2,3,5,6,7,8-hexahydro-7-methoxy-1-methyl-3-oxoisoquinoline

(1) 4-Methoxycyclohexanol

To mono-potassium salt of 1,4-cyclohexanediol which had been prepared from 17.5 g of 1,4-cyclohexanediol and 9.3 g of potassium hydroxide, 32 g of methyl iodide was added, and the resultant mixture was heated under reflux for 5 hours. After the reaction was completed, water was added and then the mixture was extracted with chloroform. The extract was subjected to distillation under reduced pressure to obtain 10.34 g of 4-methoxycyclohexanol. $b_{15}$: 100°–103° C.

NMR $\delta_{TMS}^{CCl_4}$: 1.2–2.0 (8H, m); 2.68 (1H, s); 3.0–3.2 (1H, m); 3.24 (3H, s); 3.5–3.7 (1H, m).

(2) 4-Methoxycyclohexanone

To methylene chloride there was added 11 g of pyridinium chlorochromate, and a solution consisting of 4.2 g of 4-methoxycyclohexanol and 30 ml of methylene chloride was then added. The reaction was carried out at room temperature for 3 hours. The product was purified on Florisil column. After distillation, there was obtained 3.7 g of 4-methoxycyclohexanone.

$b_{16}$: 86° C.

NMR $\delta_{TMS}^{CCl_4}$: 1.7–2.6 (8H, m); 3.34 (3H, s); 3.4–3.6 (1H, m).

(3) 2-Acetyl-4-methoxycyclohexanone

To a suspension of 60% sodium hydride (1.12 g) in 2.5 g of ethyl acetate, a solution consisting of 1.78 g of 4-methoxycyclohexanone and 0.5 ml of benzene was dropwise added. The reaction was allowed to proceed at 40° C. for 3 hours and then at room temperature for 3 hours. A small amount of methanol was added to decompose the sodium hydride. The reaction mixture was then poured into water, neutralized with hydrochloric acid, and extracted with ether. Thus, 1.16 g of 2-acetyl-4-methoxycyclohexanone was obtained.

NMR $\delta_{TMS}^{CCl_4}$: 2.06 (3H, s); 1.7–2.5 (8H, m); 3.28 (3H, s); 3.4 (1H, m); 15.9 (1H, s).

(4) 4-Cyano-2,3,5,6,7,8-hexahydro-7-methoxy-1-methyl-3-oxoisoquinoline

2-Acetyl-4-methoxycyclohexanone (1.02 g) and cyanoacetamide (0.462 g) were added to 5 ml of ethanol. After adding a small amount of piperidine, the mixture was heated under reflux for 2 hours. Deposited crystals were filtered out and recrystallized from methanol. There was obtained 0.42 g of 4-cyano-2,3,5,6,7,8-hexahydro-7-methoxy-1-methyl-3-oxoisoquinoline.

mp: 257°–259° C.

NMR $\delta_{TMS}^{CF_3COOH}$: 2.25 (2H, m); 2.57 (3H, s); 3.20 (2H, m); 3.66 (3H, s); 4.16 (1H, m).

(5) 4-Acetyl-2,3,5,6,7,8-hexahydro-7-methoxy-1-methyl-3-oxoisoquinoline

Magnesium (0.6 g) was suspended in 30 ml of ether. To the resulting suspension, 4.5 g of methyl iodide was dropwise added in such a rate that the ether was slowly refluxed. After adding 40 ml of benzene, 1.0 g of 4-cyano-2,3,5,6,7,8-hexahydro-7-methoxy-1-methyl-3-oxoisoquinoline was gradually added and the mixture was heated under reflux for 2 hours. After cooling, 10% hydrochloric acid was added while cooling on ice. The reaction mixture was then extracted with chloroform. There was obtained 0.58 g of 4-acetyl-2,3,5,6,7,8-hexahydro-7-methoxy-1-methyl-3-oxoisoquinoline.

mp: 222°–224° C. (decomposition).

NMR $\delta_{TMS}^{DMSO-d_6}$: 1.6–2.0 (3H, m); 2.16 (3H, s); 2.40 (3H, s); 2.40–2.80 (4H, m); 3.28 (3H, s); 12.25 (1H, s).

EXAMPLE 7

4-Acetyl-2,3,5,6,7,8-hexahydro-1,7-dimethyl-3-oxoisoquinoline (1) 2-Acetyl-4-methylcyclohexanone To 24 g of 40% boron trifluoride acetate complex cooled on ice, a mixture of 5.6 g of 4-methylcyclohexanone and 10.5 g of acetic anhydride was dropwise added. The resultant mixture was then stirred at room temperature for 4 hours. To the mixture there was added 50 ml of a saturated aqueous solution of sodium acetate, and then the mixture was heated under reflux for one hour. After cooling, the reaction mixture was extracted with ether to obtain 2-acetyl-4-methylcyclohexanone, which was directly used in the following step without further purifying.

(2) 4-Cyano-2,3,5,6,7,8-hexahydro-1,7-dimethyl-3-oxoisoquinoline

The crude product of the step (1) above, 2-acetyl-4-methylcyclohexanone, was dissolved in 35 ml of ethanol. To the resultant solution, there were added 3.36 g of cyanoacetamide and a small amount of piperidine, and the mixture was heated under reflux for 4 hours. Deposited crystals were filtered out and recrystallized from a mixed solvent of methanol and water. There was obtained 4.22 g of 4-cyano-2,3,5,6,7,8-hexahydro-1,7-dimethyl-3-oxoisoquinoline.

mp>300° C.

NMR $\delta_{TMS}^{CF_3COOH}$: 1.23 (3H, d); 2.60 (3H, s); 1.8–3.3 (4H, m).

(3) 4-Acetyl-2,3,5,6,7,8-hexahydro-1,7-dimethyl-3-oxoisoquinoline

To a suspension of 0.6 g of magnesium in 30 ml of ether, 4.8 g of methyl iodide was dropwise added while slowly refluxing. After adding 40 ml of benzene, there was gradually added 1.0 g of 4-cyano-2,3,5,6,7,8-hexahydro-1,7-dimethyl-3-oxoisoquinoline. Then, the mixture was heated under reflux for 2 hours. After cooling, 10% hydrochloric acid was added while cooling on ice. Deposited crystals were filtered out and washed with chloroform. Thus, there was obtained 0.8 g of 4-acetyl-2,3,5,6,7,8-hexahydro-1,7-dimethyl-3-oxoisoquinoline.

mp: 271°–273° C. (decomposition).

NMR $\delta_{TMS}^{DMSO-d_6}$: 1.6–2.0 (3H, m); 2.16 (3H, s); 2.40 (3H, s); 2.40–2.80 (4H, m); 3.28 (3H, s); 12.25 (1H, s).

EXAMPLE 8

2,3,5,6,7,8-Hexahydro-1-methyl-3-oxoisoquinoline (1) 4-Cyano-2,3,5,6,7,8-hexahydro-1-methyl-3-oxoisoquinoline 2-Acetylcyclohexanone (5 g) and cyanoacetamide (3 g) were added to 25 ml of ethanol and a small amount of piperidine was also added. The mixture was heated under reflux for 2 hours. After cooling, deposited crystals were filtered out and washed with ethanol. There was obtained 4.5 g of 4-cyano-2,3,5,6,7,8-hexahydro-1-methyl-3-oxoisoquinoline.

mp: 271° C. (decomposition).

NMR $\delta_{TMS}^{CF_3COOH}$: 1.8–2.1 (4H, m); 2.56 (3H, s); 2.6–3.2 (4H, m).

(2) 2,3,5,6,7,8-Hexahydro-1-methyl-3-oxoisoquinoline

4-Cyano-2,3,5,6,7,8-hexahydro-1-methyl-3-oxoisoquinoline (1.88 g) was dissolved in 20 ml of 85% sulfuric acid, and the resultant solution was heated at 180°–190° C. for 10 hours. After cooling, the reaction mixture was poured into ice water and an aqueous sodium hydroxide solution was added to adjust the pH to about 5. Deposited crystals were filtered out and recrystallized from methanol. Thus, there was obtained 1.28 g of 2,3,5,6,7,8-hexahydro-1-methyl-3-oxoisoquinoline.

mp: 241° C.

NMR $\delta_{TMS}^{DMSO-d_6}$: 2.2–2.6 (4H, m); 2.05 (3H, s); 5.03 (1H, s); 11.38 (1H, s).

EXAMPLE 9

2,3,5,6,7,8-Hexahydro-1-methyl-4-nitro-3-oxoisoquinoline

To a solution of 1.63 g of 2,3,5,6,7,8-hexahydro-1-methyl-3-oxoisoquinoline in 10 ml of acetic acid, 1 ml of concentrated sulfuric acid and 5 ml of concentrated nitric acid (d=1.42) were dropwise added under cooling on ice. After the reaction was completed, the reaction mixture was poured into ice water and deposited crystals were filtered out. There was obtained 1.0 g of 2,3,5,6,7,8-hexahydro-1-methyl-4-nitro-3-oxoisoquinoline. mp: 255° C. (decomposition).

NMR $\delta_{TMS}^{DMSO-d_6}$: 1.5–1.8 (4H, m); 2.21 (3H, s); 2.3–2.7 (4H, m).

The following compounds were synthesized in a similar manner to the methods of Examples 1 to 9.

EXAMPLE 10

4-Acetyl-2,3,5,6,7,8-hexahydro-1-methyl-3-oxoisoquinoline mp: 245°–247° C.

NMR $\delta_{TMS}^{CDCl_3}$: 1.6–1.8 (4H, m); 2.27 (3H, s); 2.3–2.5 (2H, m); 2.56 (3H, s); 2.6–2.8 (2H, m); 13.90 (1H, s).

EXAMPLE 11

4-Acetyl-2,3,5,6,7,8-hexahydro-1-methyl-3-oxo-7-phenylisoquinoline mp: 259°–261° C.

NMR $\delta_{TMS}^{CDCl_3}$: 1.85 (3H, m); 2.28 (3H, s); 2.58 (3H, s); 2.80 (4H, m); 7.28 (5H, s); 13.9 (1H, s).

EXAMPLE 12

4-Bromo-2,3,5,6,7,8-hexahydro-1-methyl-3-oxo-7-(4-pyridyl)isoquinoline 2,3,5,6,7,8-Hexahydro-1-methyl-3-oxo-7-(4-pyridyl)isoquinoline (0.4 g) obtained in Example 1 was dissolved in 6 ml of acetic acid, and a solution of 0.27 g of bromine and 1.3 ml of acetic acid was dropwise added at 45° C. After the reaction was completed, the reaction mixture was poured into water and an aqueous solution of sodium hydroxide was added to adjust the pH to 9–10. The deposit was filtered out and recrystallized from methanol. Thus, there was obtained 0.21 g of 4- bromo-2,3,5,6,7,8-hexahydro-1-methyl-3-oxo-7-(4-pyridyl)isoquinoline.

mp: 295°-297° C. (decomposition).

Elementary Analysis (%): C 55.88 (56.44); H 4.71 (4.74); N 8.74 (8.78); Br 24.74 (25.03)—theoretical values being in brackets.

TEST EXAMPLE 1

Pharmacological Test

Adult mongrel dogs weighing 8–12 kg were anesthetized with sodium pentobarbital (30 mg/kg, i.v.). A pressure sensor catheter was inserted via right carotid artery into left ventricule of heart to measure the left ventricular pressure (LVP). While the first derivative of LVP (LV dp/dt) was calculated by a differentiator. The right femoral artery was cannulated to measure systemic blood pressure (BP). Heart rate (HR) was recorded from the pulse wave of BP by a cardiotachograph. The drug was administered via right femoral vein and continuous propranolol infusion was carried out via left femoral vein. All parameters were simultaneously recorded on a heat transcription recorder.

Stable heart failure conditions were obtained by 4 mg/kg, i.v. of propranolol injection followed immediately by the infusion of 0.1 mg/kg/min, i.v. Such infusion technique produced significant decrease in LV dp/dt max and slight decreases in BP, HR and LVP. Effective doses (ED$_{100}$) of the test compounds sufficient enough to recover the value of LV dp/dt max before the propranolol injection were determined. Changes in BP and HR at ED$_{100}$ were shown as the change (%) against the value observed at the stable heart failure conditions.

TABLE 1

| Example No. | ED$_{100}$ (mg/kg, i.v.) | Blood Pressure (%) | Heart Rate (%) |
|---|---|---|---|
| 1 | 0.1 | −0.6 | 11.6 |
| 2 | 0.1 | −14.4 | 21.9 |
| 3 | 0.1 | −4.4 | 19.4 |
| 4 | 0.3 | −3.9 | 15.1 |
| 5 | 0.3 | −18.2 | 24.9 |

TABLE 1-continued

| Example No. | ED$_{100}$ (mg/kg, i.v.) | Blood Pressure (%) | Heart Rate (%) |
|---|---|---|---|
| 6 | 0.3 | 8.6 | 25.3 |
| 7 | 1.0 | −45.2 | 6.7 |
| 8 | 1.0 | −5.5 | 16.5 |
| 9 | 1.0 | −5.2 | 24.6 |

TEST EXAMPLE 2

Acute Toxicity

After fasting for 18 hours, each compound according to the present invention was orally administered to the mice (ddy, male, 5 weeks old, one group consisting of 5 mice). LD$_{50}$ values obtained by 7 days observation after the drug administration are not less than 600 mg/kg.

What is claimed is:

1. Isoquinoline derivatives represented by the general formula:

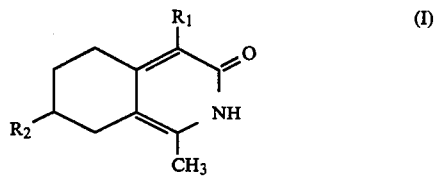

wherein R$_1$ denotes a hydrogen or halogen atom, or a nitro or acetyl group, and R$_2$ denotes a hydrogen atom, or a methyl, methoxy, phenyl, 4-pyridyl or 2-pyridyl group, and therapeutically acceptable salts thereof.

2. The compound in accordance with claim 1 which is 4-acetyl-2,3,5,6,7,8-hexahydro-1-methyl-3-oxo-7-(4-pyridyl)isoquinoline.

3. The compound in accordance with claim 1 which is 2,3,5,6,7,8-hexahydro-1-methyl-3-oxo-7-(4-pyridyl)isoquinoline.

4. The compound in accordance with claim 1 which is 4-acetyl-2,3,5,6,7,8-hexahydro-1-methyl-3-oxo-7-(2-pyridyl)isoquinoline.

5. The compound in accordance with claim 1 which is 2,3,5,6,7,8-hexahydro-1-methyl-3-oxo-7-(2-pyridyl)isoquinoline.

* * * * *